(12) United States Patent
Aoki

(10) Patent No.: US 6,927,234 B2
(45) Date of Patent: Aug. 9, 2005

(54) XANTHONE DERIVATIVES, METHOD OF PRODUCTION THEREOF, AND PHARMACEUTICAL COMPOSITION CONTAINING THE SAME

(75) Inventor: Henry Aoki, Lacton, MA (US)

(73) Assignee: Kuboyama Bio Ken Inc., Tokyo (JP)

( * ) Notice: Subject to any disclaimer, the term of this patent is extended or adjusted under 35 U.S.C. 154(b) by 90 days.

(21) Appl. No.: 10/716,732

(22) Filed: Nov. 19, 2003

(65) Prior Publication Data

US 2005/0070590 A1 Mar. 31, 2005

Related U.S. Application Data (60) Provisional application No. 60/506,229, filed on Sep. 26, 2003.

(51) Int. Cl.⁷ .................. A61K 31/409; A61K 38/08; C07D 407/02
(52) U.S. Cl. .................. 514/410; 424/185.1; 514/17; 548/421; 549/383
(58) Field of Search .............. 514/410, 17; 424/185.1; 548/421; 549/383

(56) References Cited

U.S. PATENT DOCUMENTS

| | | |
|---|---|---|
| 4,776,104 A | 10/1988 | Kuoyama ............ 34/77 |
| 5,170,697 A | 12/1992 | Kuboyama ............ 99/470 |
| 5,572,923 A | 11/1996 | Kuboyama ............ 99/287 |
| 5,741,813 A | 4/1998 | Lin et al. ............ 514/455 |
| 6,403,636 B1 | 6/2002 | Reutrakul et al. ............ 514/453 |

*Primary Examiner*—Joseph K. McKane
*Assistant Examiner*—Susannah E. Lee
(74) *Attorney, Agent, or Firm*—Nields & Lemack (57) ABSTRACT

Biologically active xanthone derivatives, as well as compositions prepared from such derivatives, possessing anti-cancer activity, anti-inflammatory activity, anti-obesity activity, and/or hair growth promotion activity, and a method for producing such derivatives and compositions. The derivatives are obtained by utilizing a heating, extracting and condensing system that efficiently recovers the derivatives from a raw material.

7 Claims, 9 Drawing Sheets

XANTHONE DERIVATIVES, METHOD OF PRODUCTION THEREOF, AND PHARMACEUTICAL COMPOSITION CONTAINING THE SAME

This application claims priority of Provisional Appln. Ser. No. 60/506,229 filed Sep. 26, 2003, the disclosure of which is hereby incorporated by reference.

BACKGROUND OF THE INVENTION

The present invention relates to novel xanthone derivatives, a process of preparing the same, pharmaceutical compositions comprising the same, and their use as pharmaceuticals, hair growth promotion agents, weight reduction and anti-obesity agents, and anti-inflammatory agents. The derivatives are particularly useful as pharmaceuticals for treating and/or preventing a variety of diseases and conditions, including sarcoma and inflammatory conditions. The derivatives, together with xanthone proper and a certain peptide, are extracted and isolated from mung bean.

Apparatus disclosed in U.S. Pat. Nos. 5,572,923, 5,170,697 and 4,776,104, the disclosures of which are herein incorporated by reference, include extraction systems for extracting an effective ingredient from a material such as malt, soybean or the like. Such apparatus comprises a pulverizing minute particle generating tank including means for heating a reservoir of water to a predetermined temperature and a means for pulverizing or atomizing water; an extracting device connected to the pulverizing minute particle generating tank, which extracting device holds a raw material layer for adhering an effective ingredient of raw material to the pulverized minute particles as the pulverizing minute particles pass through the raw material layer; a condensing device connected to the extracting device for liquefying the pulverized minute particles that have passed through and extracted an effective ingredient from the raw material layer; a reserve tank into which the water liquefied at the condensing device empties; a blower provided in a path between the reserve tank and the pulverizing minute particle generating tank for decompressing the raw material layer within the extracting device; and a cooling means for cooling the condensing device and the reserve tank.

A process whereby the liquid extract prepared from the foregoing apparatus, and/or the extract prepared from apparatus having improved condensers and/or improved drying, can be easily solidified such as by drying or freeze drying, is disclosed in co-pending U.S. Ser. No. 09/981,064, the disclosure of which is hereby incorporated by reference. Pharmaceutical compositions as well as other compositions useful in the preparation of cosmetics, perfumes and/or flavor enhancers, can be readily prepared from the solidified or dried extract. In addition, analysis of the dried extract is facilitated by using a non-nutritional absorbent material to solidify the extract compared to analysis of the extract itself.

The present inventor has now discovered that certain novel biologically active xanthone derivatives extracted from mung bean have anticancer activity, anti-inflammatory activity, anti-obesity activity, and are hair growth promoting agents.

SUMMARY OF THE INVENTION

The problems of the prior art have been overcome by the present invention, which provides biologically active xanthone derivatives, as well as compositions prepared from such derivatives, possessing, inter alia, anti-cancer activity, anti-inflammatory activity, anti-obesity activity, and/or hair growth promotion activity, and a method for producing such derivatives and compositions. The derivatives of the present invention are obtained by utilizing a heating, extracting and condensing system that efficiently recovers the derivatives from a raw material. Preferably the condenser is made up of at least two preferably cylindrical containers, with at least one container having a cooling medium therein for condensing moisture from an air stream. An optional third container can be added. The resulting liquid extract is contacted with an absorbent material, and the now extract-soaked material is dried. Alternatively, a plant or animal food material is soaked in the extract and is then dried.

BRIEF DESCRIPTION OF THE DRAWINGS

FIGS. 4($a$), ($b$) and ($c$) are perspective views showing the construction of the internal cylinder of an extracting device used to extract the active ingredient(s) in accordance with the present invention;

DETAILED DESCRIPTION OF THE PREFERRED EMBODIMENTS

The preferred raw material that can be subjected to the extraction system to produce an extract including the novel xanthone compounds in accordance with the present invention is mung bean ("phaseoulus aurcus").

Figure 1:
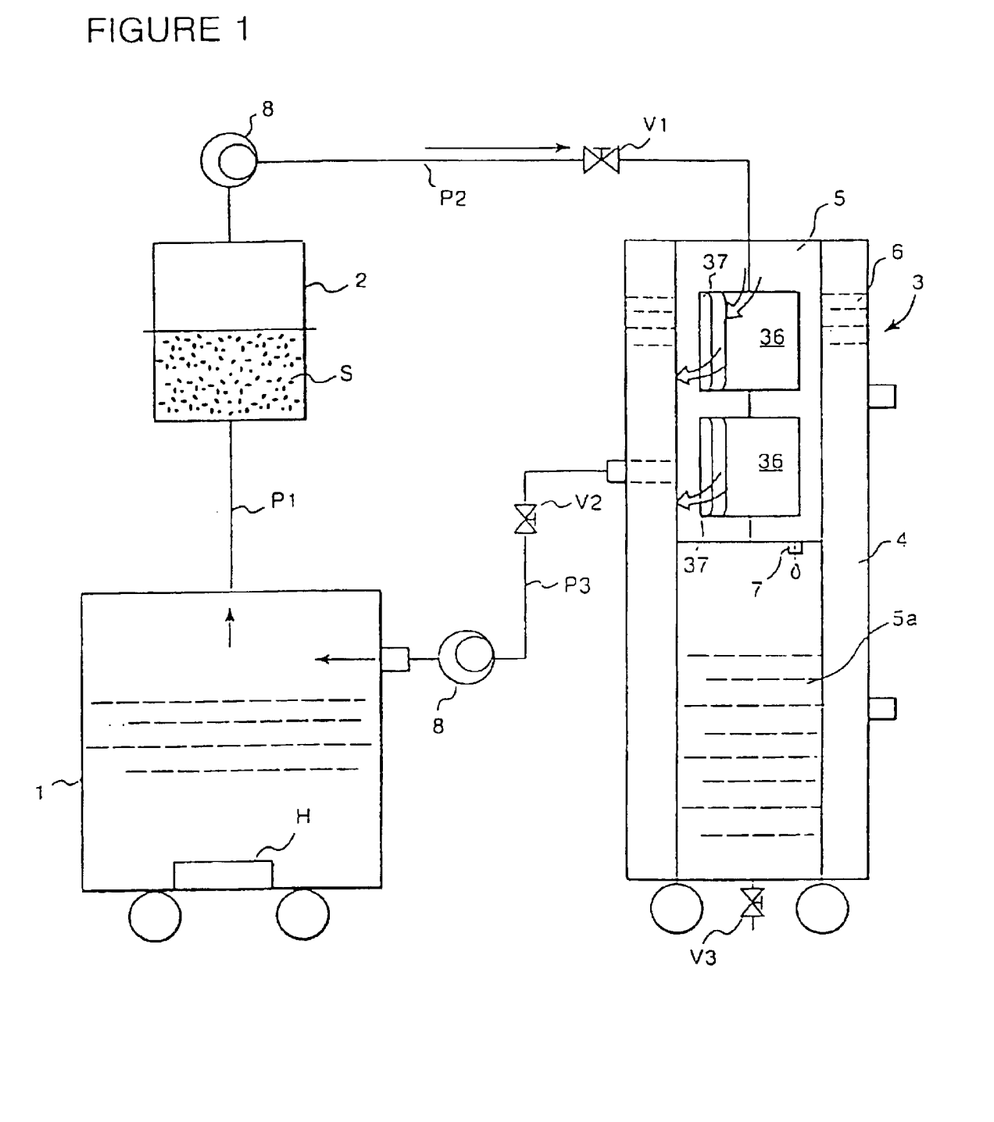
FIG. 1 is a schematic view of one embodiment of an extraction/drying apparatus used to extract the active ingredient(s) in accordance with the present invention.

Hereinafter, a preferred method of obtaining the extract will be described in more detail with reference to the accompanying drawings. FIG. 1 is a schematic view showing a construction of a first embodiment of the manufacturing apparatus, and in the drawing, reference numeral 1 is a housing or container having a reservoir of liquid, preferably water, therein. The housing 1 is preferably made of stainless steel. The size of the housing 1 is not particularly limited, and in the extraction embodiment shown, generally depends upon the amount of raw material 4 used and the desired rate of extraction of effective ingredient therefrom. The housing 1 includes means H for heating the reservoir, which means is not particularly limited, and can include an electric heating element or coil, a UV or IR heating element, a burner, etc. The heating means H must be sufficient to heat the liquid in the housing 1 to a temperature necessary to cause vaporization of the liquid. The heater can be coupled to a gauge (not shown) to allow the operator to specify the desired liquid temperature, and to a switch (not shown) to activate the heater. The heating means H can be located inside or outside of the housing 1. Means (not shown) can be optionally provided in association with the housing 1 to generate pulverized minute particles of water or a mist. Suitable means include an ultrasonic wave generating device comprising one or more sets (depending upon the tank size) of vibrators provided at the bottom of housing 1, each vibrator having the ability to pulverize water and create a mist. Conventional ultrasonic wave generators that are used in domestic ultrasonic humidifiers are suitable. Centrifugal atomization could also be used.

Figure 3:
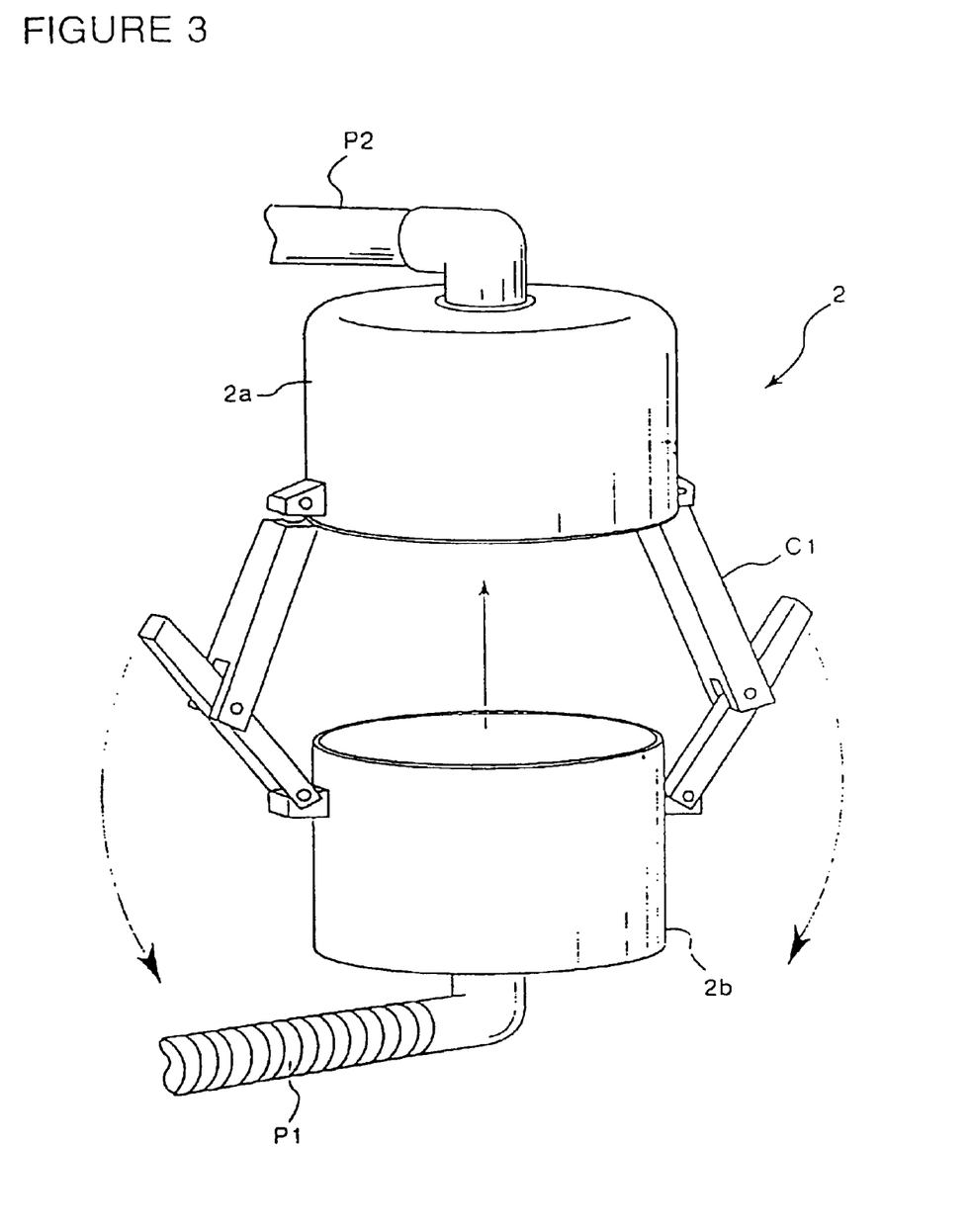
FIG. 3 is a fragmentary perspective view of an external cylinder of an extracting device used to extract the active ingredient(s) in accordance with the present invention.

Housing 1 is in fluid communication via pipe P1 or the like with an extracting device 2 for extracting an effective ingredient from raw material S contained therein. FIG. 3 is a perspective view of the external appearance of the external cylinder which is the main element of the extracting device 2, and it includes a first external cylinder 2a and a second external cylinder 2b, both of which are constructed so as to be releasably joined to one another, and are preferably made of stainless steel. A temperature sensor (not shown) for detecting the temperature during the extraction operation can be fixed to the bottom side of the second external cylinder 2b. A hinged locking mechanism C1 joins cylinder 2a to cylinder 2b so that the raw material can be easily loaded and unloaded therefrom. FIG. 3 shows the extracting device 2 in its open, unlocked position.

Figure 4A:
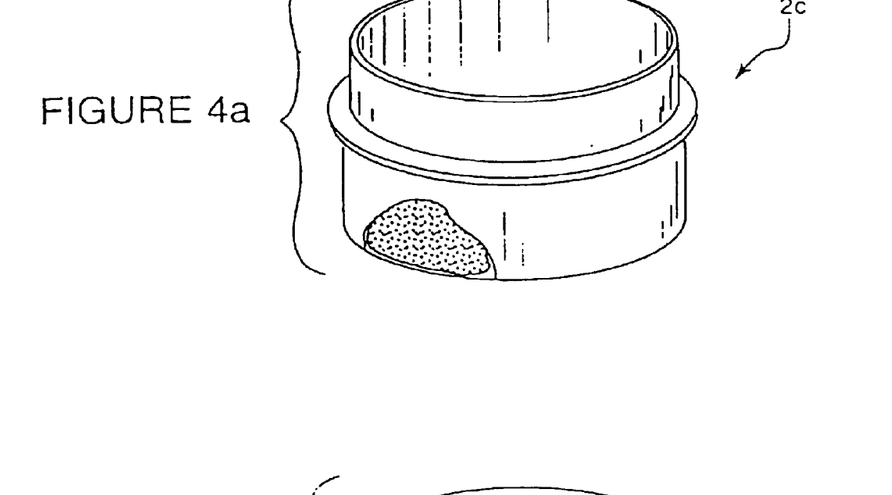
Figure 4B:
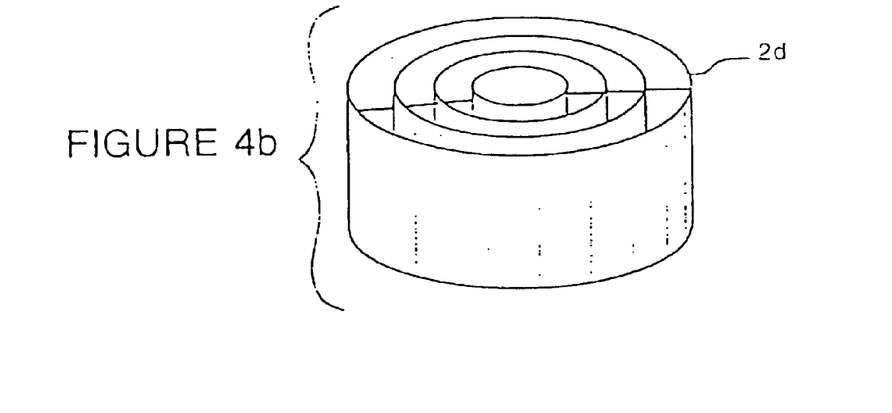
Figure 4C:
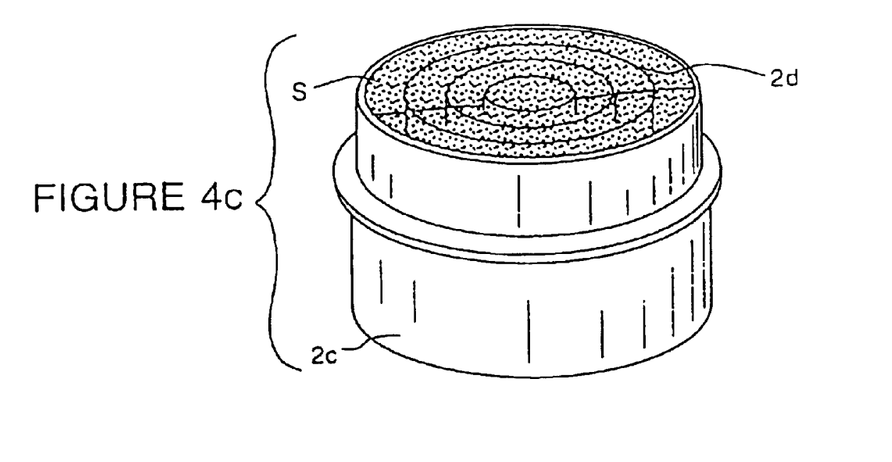

FIG. 4 is a schematic diagram of the internal cylinder that is housed in the external cylinder 2 of FIG. 3. FIG. 4(a) shows internal cylinder 2c, which is of a suitable shape and size to fit into the aforementioned external cylinder 2, and includes at the bottom thereof a net portion for holding the raw material that has been crushed into small pieces. FIG. 4(b) shows a guide plate 2d for insertion into the internal cylinder 2c, and as shown in FIG. 4(c), it is constructed so as to partition the crushed pieces S of raw material such as coffee grounds in the interior of the internal cylinder 2c. The presence of this guide plate 2d allows the vaporized liquid from the housing 1 to easily and smoothly pass through the crushed pieces S of raw material as will be described below. Those skilled in the art will appreciate that other shapes for guide plate 2d may be used, such as a spiral shape.

The extracting device 2 is in fluid communication with condensing device 3 via pipe P2. A valve V1 can be positioned in pipe P2, and together with valve V2 in pipe P3 (discussed below), regulates the airflow to and the degree of decompression in condensing device 3. The extract can be cooled in condensing device 3 by various means, including by air cooling or liquid cooling, as disclosed in U.S. Pat. Nos. 5,572,923 and 5,170,697 the disclosures of which are hereby incorporated by reference.

One embodiment of condensing device 3 is comprised of two concentric cylinders; the outer cylinder 4 housing a cooling material to cool the contents of the inner cylinder 5. In the embodiment shown, the inner and outer cylinders are not co-extensive, thereby allowing for a lower inner portion 5a for collection of liquid condensate resulting from the cooling process. However, those skilled in the art will appreciate that the inner and outer cylinder 5 can be co-extensive, with suitable means (such as tubing in communication with the inner cylinder 5 at one end and with a supplementary container at the other) provided for condensate collection elsewhere. Similarly, the inner cylinder 5 could be smaller in length than the outer cylinder 4 in order to allow the cooling material contained in the outer cylinder 4 to surround not only the sides of the inner cylinder 5, but also the bottom thereof. In this latter embodiment, suitable means would again be provided for collecting the condensate elsewhere.

Preferably the cooling material 6 contained in the outer cylinder 4 is a liquid, such as water. However, the cooling material 6 can also be a gas or a solid such as ice or other material that can maintain a cold temperature for an extended period of time. The cooling material 6 can be circulated in the outer cylinder 4 to enhance cooling, and can be continuously or continually replenished during operation.

Figure 5:
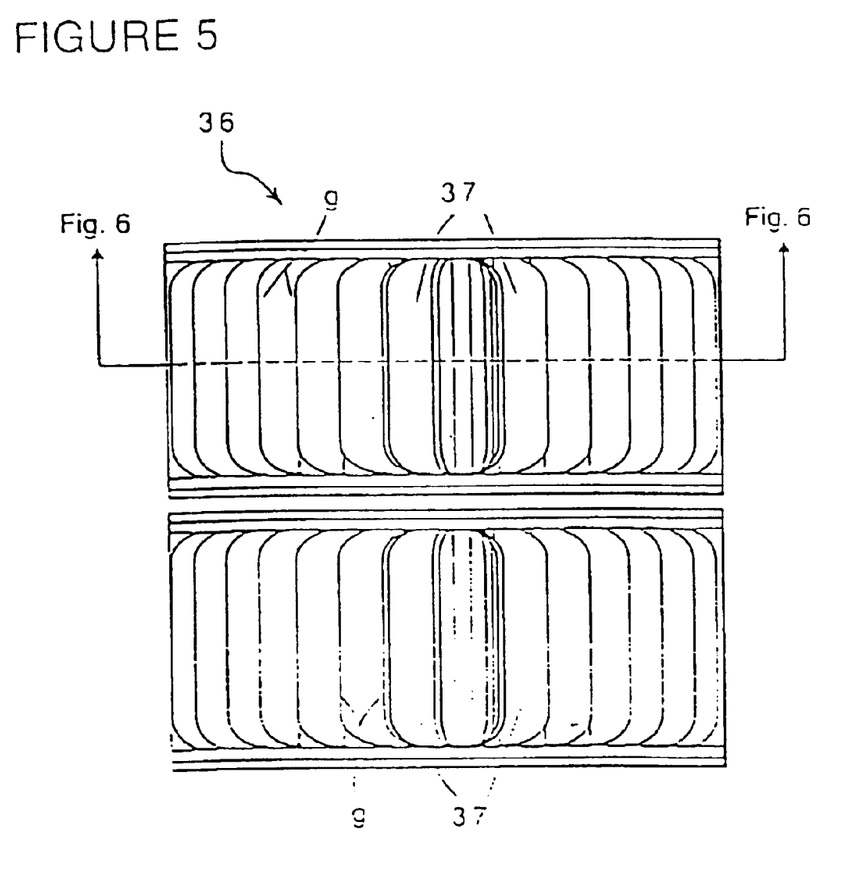
FIG. 5 is a plan view of air flow regulating means used in the extraction device used to extract the active ingredient(s) in accordance with the present invention.
Figure 6:
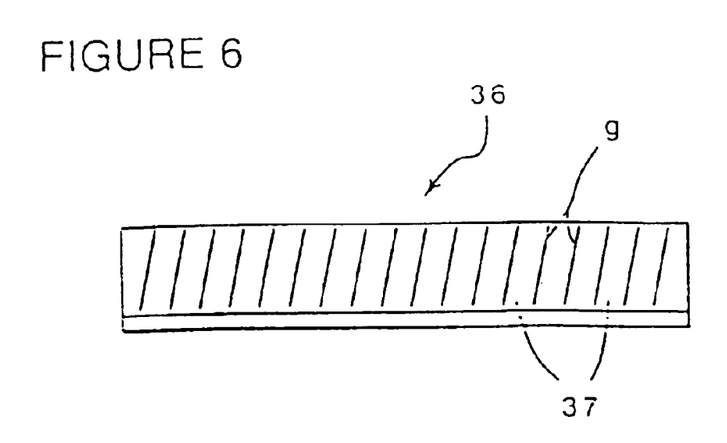
FIG. 6 is a section view taken along lines 6—6 of FIG. 5.

Preferably the inner cylinder 5 contains one or more airflow regulator means 36, most preferably two as shown. As illustrated in FIGS. 5 and 6, the air flow regulators 36 comprise a plurality of sloping plates 37 with a gap "g" formed between adjacent sloping plates 37. By adjusting the inclination of the sloping plates 37, it is possible to adjust the quantity of the airflow being regulated. Air flowing into the inner cylinder 5 causes the air flow regulators 36 to rotate about a vertical axis, thereby forcibly directing the air flow toward the wall of the cylinder 5 which is cooled by the cooling material 6 in the outer cylinder 4. Alternatively, the airflow regulator(s) 36 can be driven by a motor or the like to increase the extraction of the moisture from the air stream. Resulting condensate is drained from drain 7 and is collected.

Figure 7:
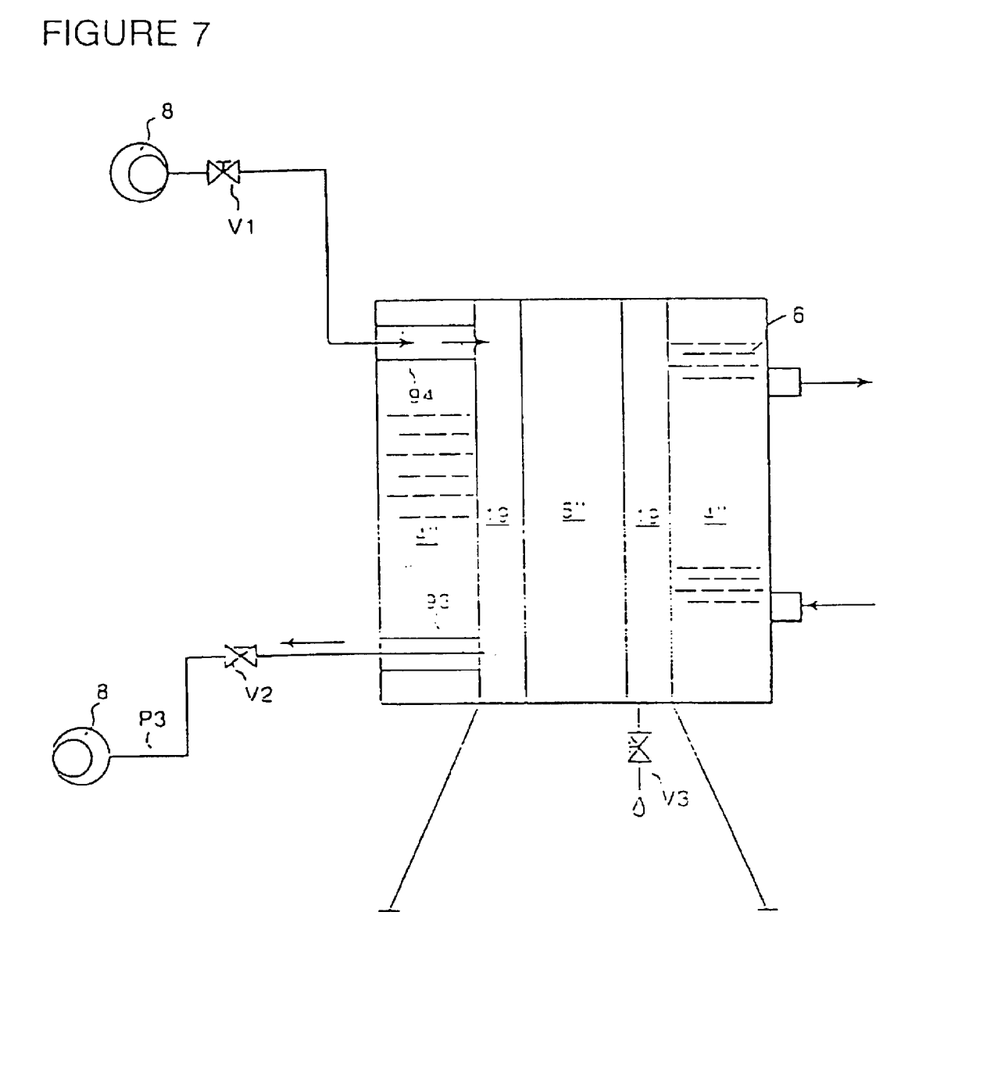
FIG. 7 is a schematic view of an embodiment of a condensing device used in an extraction system used to extract the active ingredient(s) in accordance with the present invention.

FIG. 7 illustrates an alternative embodiment of the condensing device 3 where airflow regulation is accomplished using a triple container design or the like. The outer container 4" contains a cooling material 6 in its annulus, as in the previous embodiments. The middle container M receives the air flow from the extracting device via suitable piping 94, and the air flow proceeds out of the device (and optionally is recycled back to housing 1) via pipe 93. A central container 5" is positioned so as to assist in directing the contents of the middle container M against the outer container 4" to enhance cooling. The shape of the containers are preferably cylindrical but need not be; other shapes are suitable as long as cooling is enhanced such as by forcing the air in the middle container M against the outer container 4". Surface area of the cooling walls is also important; thus a zig-zag shape could be used to increase surface area; or alternating projections could extend from the cooling walls to increase the surface area thereof.

Figure 8:
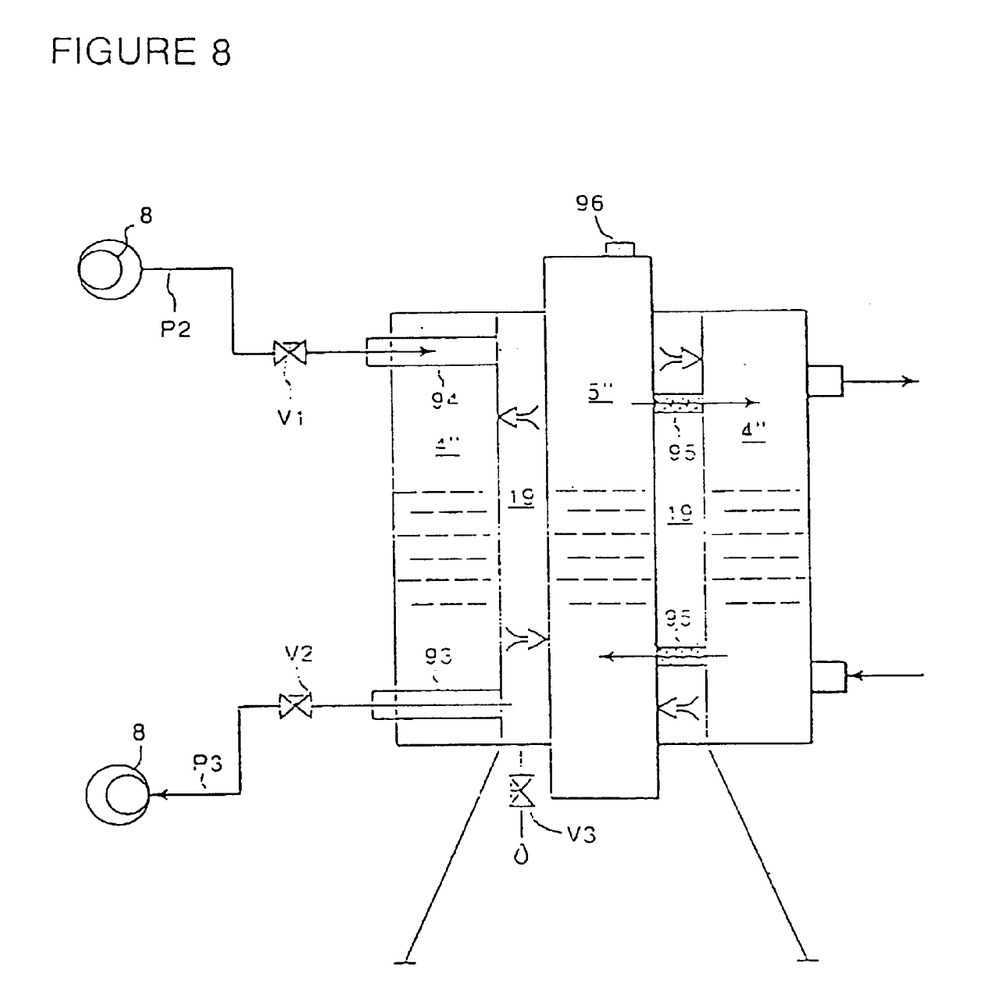
FIG. 8 is a schematic view of a condensing device used in an extraction system used to extract the active ingredient (s) in accordance with the present invention.

FIG. 8 illustrates a still further alternative embodiment of the condensing device. This embodiment is similar to that shown in FIG. 7, except the central container 5" is filled with a cooling fluid, which can be the same or different from the cooling fluid contained in the outer container 4". Where the fluid is the same, connecting means 95 can be provided between the central container 5" and the outer container 4" to circulate the cooling fluid therebetween. As in the embodiment of FIG. 7, the central container 5" is preferably but need not by cylindrical; other shapes that enhance cooling by increasing the surface area of the cooling surfaces and assist in forcing the medium to be cooled against the cooling surfaces can be used. The central container 5" can also be made shorter so that the medium to be cooled is also exposed to the bottom of the container. In addition, the inlet and outlet for the medium to be cooled can be located so that the medium to be cooled travels around the perimeter of the central container 5" prior to its exit from the condensing device. As in from FIG. 9, the central container 5" also can be longer than the outer container 4" and middle container M, and includes an inlet 96 for introducing the cooling fluid therein. The condensing device can be combined with a heater to increase the temperature of the medium from which moisture is being removed. A plurality of the devices can be arranged in series to enhance condensing, and can be arranged in series either vertically or horizontally, depending in part on space considerations. The device is easier and faster to manufacture than the embodiment of FIG. 2 using the rotary device to regulate airflow.

Figure 2:
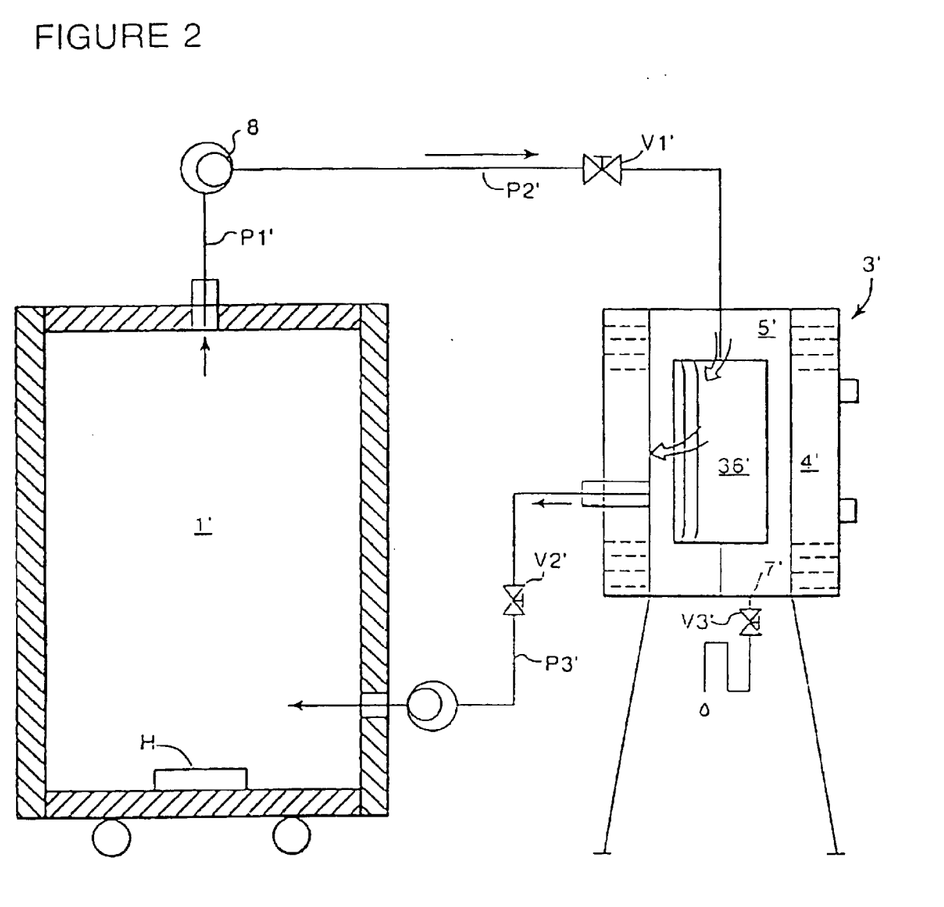
FIG. 2 is a schematic view of another embodiment of the extraction/drying apparatus used to extract the active ingredient(s) in accordance with the present invention.
Figure 9:
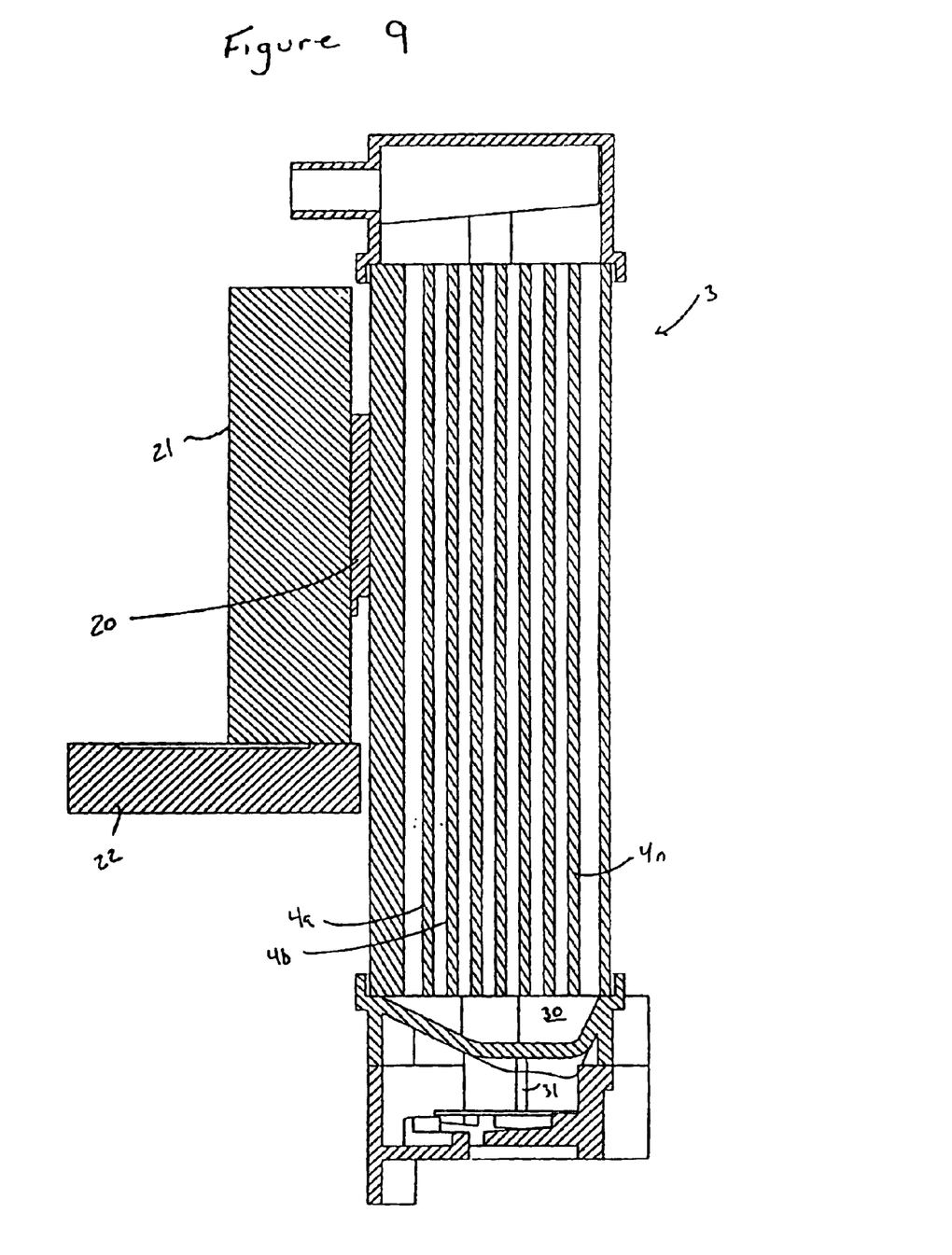
FIG. 9 is a cross-sectional view of the condensing portion of a condensing device used in an extraction system used to extract active ingredient(s) in accordance with another embodiment of the present invention.
Figure 10:
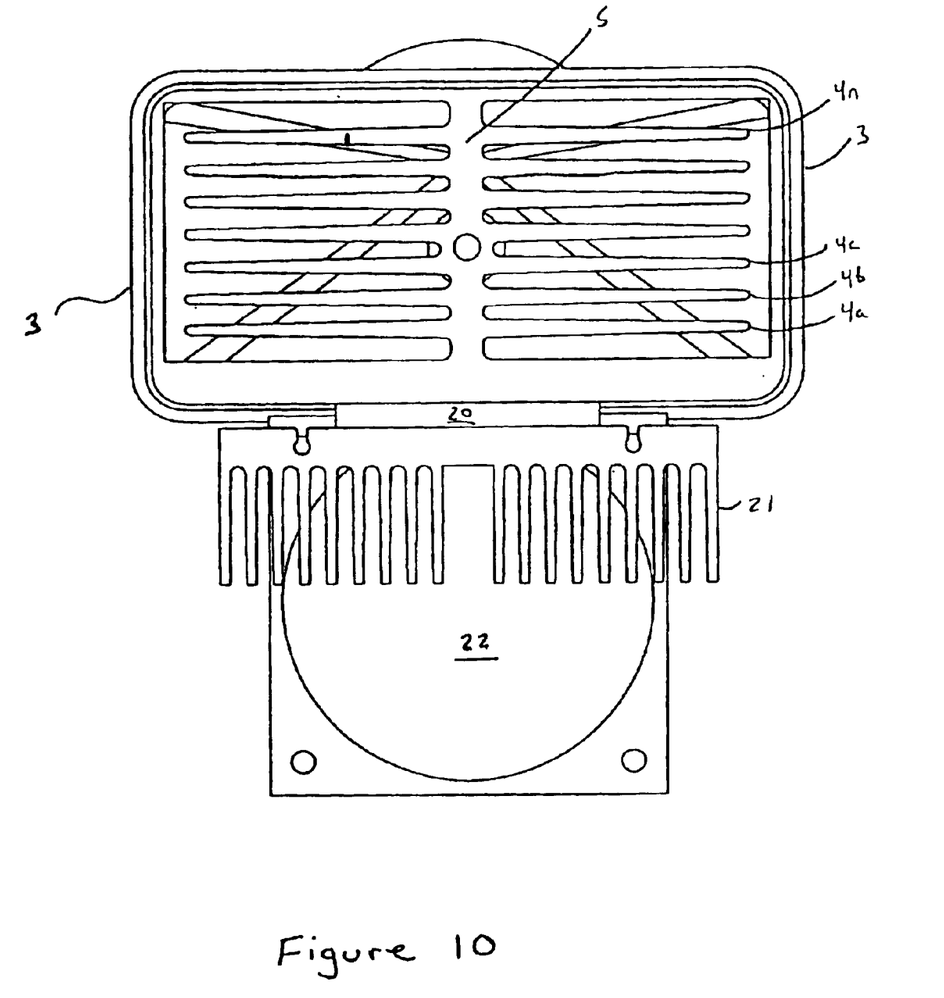
FIG. 10 is a top view of the condensing portion of the device of FIG. 9.

With reference to FIGS. 9 and 10, another embodiment of a condensing device 3 is shown. This condensing device 3 comprises a housing, which can be plastic, having one or more spaced cooling surfaces 4a–4n therein, preferably in the shape of fins as shown. The cooling surfaces 4a–4n can be made of any heat-conducting material, preferably metal, most preferably aluminum. The cooling surfaces 4a–4n preferably extend through the majority of the housing 3, providing extensive surface area within the housing for contact with the incoming material as described in detail below. The number of spaced cooling surfaces 4a–4n is not critical, it will depend upon the size of the condensing device 3 housing as well as the desired optimal rate of condensation. Preferably the cooling surfaces 4a–4n taper towards their free ends as shown. In the preferred embodiment, the cooling surfaces 4a–4n include a co-extensive divider 5 to divide the condensing device housing into two separate compartments or zones; one for flow of the incoming material, the other for recycle flow of outgoing material not condensed by the condensing device 3. More specifically, incoming material from pipe P2 flows downwardly (based on the orientation of the apparatus as shown in FIG. 2) into a first compartment where it contacts cooling surfaces 4a–4n positioned therein. Any material not condensed then crosses from this first compartment to the second compartment in the condensing chamber 30 where the two compartments communicate, and then flows upwardly (again with respect to the orientation of the apparatus as shown in FIG. 2) through the second compartment where it contacts the cooling surfaces 4a–4n positioned therein. Any material not condensed in the second compartment flows out pipe P3 and is recycled to container 1 via fan 8.

Cooling of the cooling surfaces 4a–4n is accomplished with one or more thermoelectric coolers 20 conventional in the industry. Briefly, the thermoelectric coolers are solid state heat pumps, whereby the flow of DC current through the cooler causes heat transfer, creating a cold side and a hot side. The thermoelectric cooler(s) 20 are placed in heat-conducting relationship with the cooling surfaces 4a–4n, such as by including the use of thermal conductive grease or the like. The coolers 20 are positioned such that the cold sides thereof cool the cooling surfaces 4a–4n. Depending upon the desired cooling, a modular design can be used containing multiple thermoelectric coolers 20. Preferably a heat sink 21 is also placed in heat-conducting relationship with the thermoelectric cooler(s) 20 so as to dissipate heat therefrom. A fan 22 can be used in proximity to the heat sink 21 to enhance the dissipation of heat as shown.

The present inventor has found that the amount of condensate produced by the condensing device 3 including the thermoelectric cooler(s) 20 is efficiently optimized if the temperature of the cooling surfaces 4a–4n is between 3° C. and 60°. Suitable temperature ranges also include 10–60° C. and 30–55° C. Temperatures at the lower end of the range require multiple thermoelectric coolers, and therefore a larger heat sink, more fan capacity and more electricity to power the cooler and fan.

Condensate resulting from the cooling in the condensing device 3 flows into a condensing chamber 30 located at the lower end of condensing device 3 below the point at which the cooling surfaces 4a–4n terminate. From the condensing chamber 30, the condensate flows into a drain pipe 31 where it is directed into an extract reservoir where it is collected. Any vapor not condensed is recycled via pipe P3 and fan 8 to the container 1 for further processing.

At least one or more (two shown) air circulating or driving means is provided, preferably in the form of a fan or blower 8. The fan(s) 8 should be of a sufficient size so as to create decompression and provide flow through the system. The decompression should be within the range of about 5 to 500 mm $H_2O$. A conventional domestic vacuum cleaner fan has been found to be effective.

The condensing device 3 is in communication with housing 1 via pipe P3. Valve V2 can be positioned in pipe P3 to regulate airflow and decompression with valve V1. For example, if valve V1 is partially closed while valve V2 is open, then the condensation apparatus 3 will be under a state of decompression. If valve V2 is partially closed while valve V1 is open, the pressure in the condensation apparatus 3 will increase. The modulating of the valves can be accomplished manually or automatically.

The operation of the apparatus will now be described based upon the above construction.

First, the raw material is crushed to a magnitude approximating rice grains by any suitable means and is filled into the internal cylinder 2c illustrated in FIG. 5(a). Once filled, the net is placed over the raw material in order to stably maintain it in the internal cylinder 2c.

Successively, the internal cylinder 2c is inserted into the external cylinder 2 shown in FIG. 3. The housing 1 is filled with a sufficient amount of water or other liquid so that a mist can be produced. The water can be maintained at the same level continuously, or can be added batchwise. The temperature gauge is set to the desired temperature, and the heater is activated to heat the water to a suitable temperature such that the temperature in the extracting device 2 is at such a level (generally below 100° C.) as to not destroy the effective ingredients of the raw material. For example, in the case of mung beans and soybeans, the temperature of the water is preferably heated to about 85° C., so that the temperature of the water when it reaches the extracting device is between about 60–70° C., preferably about 65° C.

Once the water temperature in the housing 1 reaches the desirable level, the blower(s) 8 is activated to initiate flow through the system. The blower(s) 8 causes air flow to circulate in the closed circulating path formed by the housing 1, the extracting device 2 and the condensing device 3, as well as the pipes connecting these respective devices. The mist of water generated in the housing 1 thus pass through pipe P together with the airflow and reaches the extracting device 2. The temperature in the extracting device 2 can be measured by a temperature sensor to ensure that the appropriate temperature is reached therein. The temperature in the housing 1 can be controlled in response to the temperature in the extraction device 2.

As described above, the airflow is circulated between each device by the operation of the blower(s) 8, but since the extracting device 2 is filled with the crushed particles S of raw material, the raw material creates a resistance to the air flow, thereby creating a decompressed space within the extracting device 2.

Once the decompressed state is achieved, ingredients within the raw material are extracted to the surface of the crushed pieces S of raw material, and are then captured by the mist of water passing therethrough. Since the temperature within the extracting device, and more particularly, the temperature within the internal cylinder 2c is maintained within the desired range, the ingredients contained in the raw material are extracted into the water without being destroyed by heat.

The resulting liquid (e.g., water) containing the effective ingredient of the raw material then flows to the condensing device 3 through the connecting pipe P2 together with the airflow from the blower 8. The outer cylinder 4 of the condensing device 3 is filled with cooling material, preferably water, at a temperature sufficient to cause condensation of the water in the inner cylinder 5. Airflow and decompression in condensing device 3 are controlled by modulation of valves V1 and V2. The liquefied or condensed material drains through drain 7 as shown, and can be ultimately collected through valve V3.

The particles that are not liquefied in the condensing device 3 are sucked towards the housing 1 through the connecting pipe P3 together with the airflow, and are thereby recycled. The recycled portion optionally can be preheated such as by a rectifying plate or spiral shape, so as not to lower the temperature of the water in the tank 1.

The cooling material in the condensing device 3 can be changed periodically. Alternatively, a continuous flow of cooling liquid can be used to cool the inner cylinder 5.

The raw material can be crushed to about the size of rice grain. However, the concentration of effective ingredient contained in the final product can be controlled by varying the size of the raw material. For example, if the raw material is crushed into fine pieces, a final product high in effective ingredient concentration can be obtained. However, in such a case the rate at which the final product is produced decreases. As the size of the raw material increases, the concentration of effective ingredient in the final product decreases, and the rate of production increases. Similarly, the use of the guide plate 2d increases the yield of final product per hour by about 20%, but the concentration of effective ingredient in the final product decreases.

With the foregoing apparatus described in each of the embodiments, it is possible to obtain balanced drying without influence from external air by circulating moisture-laden air through a condensing device to reduce or eliminate the moisture content thereof. The result is a substantial reduction in drying time and concomitant energy requirements therefor.

The product is a colorless, transparent and clear liquid. The extract is then solidified. In a first embodiment, the procedure for solidification is as follows.

A non-nutritional material that is absorbent is used. Suitable materials include hydrophilic membrane filters such as modified polyvinylidene fluoride membranes such as the Durapore® filter commercially available from Millipore Corporation, glass fiber membranes, cotton, nylon, cellulose, or paper material such as that used in tea bags. The form of the material is not particularly limited, and can include sheets add discs. The particular identity of the material chosen for a given application will depend in part upon the nature of the solvent used in a subsequent process, such as an analysis process used to identify the ingredients of the final product.

The absorbent material is contacted with the extract. Preferably the entire surface of the absorbent material is wetted with the extract. In the case where the absorbent material is a filter, complete wetting of the material with the extract can be accomplished by using a driving force to push or pull the extract through the filter, such as pressure or vacuum (using a vacuum pump, for example). The absorbent material optionally can be heated, before or during wetting with the extract, to expand the pores and enhance wetting. Alternatively or in addition, the extract can be heated, alone or together with the absorbent material.

Once the absorbent material is sufficiently wetted with the extract, the extract is adhered to the filter preferably by drying. Drying can be accomplished by freeze-drying, heating or air-drying, with freeze-drying being particularly preferred. The dried material can be stored for significant lengths of time without deterioration of the extract. It can be dissolved in water or a suitable solvent, resulting in the dissolution of the extract's effective ingredient in water or the solvent. Increased pressure can be used to facilitate dissolution, if desired. The dried material also can be subjected to analysis, particularly analysis for pharmaceutical research, or first dissolved and then the resulting solution subjected to analysis. If the absorbent material used was a paper, the dried material can be dissolved in water and ingested as a health drink.

In the event freeze-drying is used, the freeze-drying process is preferably carried out at a temperature ranging from about −10° C. to about −70° C. and at a vacuum of about 5.3 cfm to about 23 cfm displacement. Those skilled in the art will appreciate that the temperature and the vacuum can vary depending upon the nature of the material and the size of the material, as well as the particular freeze dryer used. The amount of time the material is subjected to freeze-drying can be readily determined by the skilled artisan and depends in part on the concentration of the material.

The resulting product can be stored for long lengths of time, spanning many days or months, without deleteriously affecting the quality or taste of the product. Indeed, the taste of the resulting product, upon reconstitution with water or other liquid carrier, is enhanced compared to the original raw material. Transportation and storage are facilitated and made more cost effective. The effective ingredients in the extract, which are otherwise may be destroyed by heating, are preserved by using the extraction process detailed above. The freeze-dried product also has a longer shelf life than the liquid extract, and lends itself to chemical identification and testing.

The freeze-dried product can be reconstituted simply by adding a liquid carrier, preferably water, to the product. The amount of liquid carrier to be added is not particularly limited, and depends on the desired concentration of extract in the final potable liquid. It can be used as is (i.e., without reconstitution) as an additive for or with other foods, such as a garnish for salad, a dried soup ingredient, or mixed with other food ingredients. The freeze-dried product can be heated so that vaporized aroma can be distributed in a room.

The xanthone derivatives of the present invention, extracted from mung bean in accordance with the foregoing method, is represented by the following formula:

and include isomers, stereoisomers, and physiologically acceptable salts or solvates thereof and mixtures thereof. The extract obtained from the above process also comprises xanthone itself, as well as a peptide having the amino acid sequence tyrosine-isoleucine-glycine-serine-arginine (Tyr-Ile-Gly-Ser-Arg).

The pharmaceutical compositions containing an effective amount of the xanthone derivative are useful as human and animal drugs, such as for the treatment and/or prevention of various diseases and conditions, including cancer and anti-inflammatory conditions. An effective amount for treating a patient is the amount of the compound that, upon administration to a patient in need thereof, inhibits the progression of cancer, reduces or eliminates the volume or size of tumors, kills malignant cells, reduces or eliminates inflammation, results in the loss of weight, and/or promotes the growth of hair. The various diseases against which the xanthone derivatives are effective include various types of cancer, AIDS, SARS, malaria and brain disorders. The various types of inflammation against which the xanthone derivatives are effective include encephalitis, cerebral meningitis, marginal blepharitis, conjunctivitis, keratitis, iritis, retinitis, stomatitis, cheilitis, glossitis, tonsillitis, internal otitis, external otitis, otitis media, gastritis, duodenitis, pneumonia, pleurisy, bronchitis, rhinitis, colitis, inflammation of the small intestine, nephritis, pyelitis, pancreatitis, cholecystitis, hepatitis, thyroiditis, prostatitis, cystitis, myotis, periostitis, osteomyelitis, orchitis, endometritis, vaginitis, ovaritis, dermatitis, arthritis, periproctitis, lymphadenitis, diabetes (inflammation of the pancreatic islets), common cold (tonsillitis, bronchitis, rhinitis, mucositis), urticaria, various kinds of eczema (dermatitis), nephrosis (nephritis), alveolar pyorrhea (parodontitis, aplicalis, endodontitis), asthma (bronchitis), neuralgia (neuritis), lung tuberculosis (pneumonia, bronchitis, mucositis), infectious diseases (inflammation, induced by bacteria and virus), allergy (inflammation induced by antigen-antibody reaction), leprosy (viral dermatitis, and myotis), cancer (inflammation and fibroid induration are also causes), ulcer (progression of inflammation), fibroid induration (progression of inflammation and ulcer), reduced energy (adenitis), keratosis, collagen diseases, hysteria, neurosis, liver cirrhosis, hypertension, thrombosis, angina, rheumatism, gout, stiffness, Alzheimer, Lyme diseaes, mad cow disease, and inflammation due to parasites.

The magnitude of the therapeutic or prophylactic dose of the extracts of the present invention in the treatment or prevention of disease will depend in part upon the identity, severity and nature of the condition being treated. The dose and the frequency of the dosing will also vary according to age, body weight and response of the particular patient. In general, the total daily dose range for the xanthone derivatives of the present invention is from about 1 to about 10 mcg/kg of body weight at least once daily, preferably two to three times a day. The dose for more severe conditions can be from about 10 to about 100 mcg/kg body weight, at least once daily. Frequency of dose can be as high as about three to four times daily if necessary or desired.

Any suitable route of administration well known to those skilled in the art may be employed to provide an effective dosage of the xanthone derivatives of the present invention, including oral, intravenous, intramuscular, intradermal and subcutaneous, although oral administration is preferred, most preferably in liquid form. For hair growth promotion, the derivatives can be applied in topical form, including as a liquid, gel, cream, salve, emulsion, etc.

The pharmaceutical compositions of the present invention may be combined with other therapeutic agents, such as analgesics.

The pharmaceutical compositions of the present invention are administered to animals, including dogs, cats, fish and humans. The compounds of the present invention can include pharmaceutically acceptable carriers and other conventional additives, including aqueous based carriers, co-solvents such as ethyl alcohol, propylene glycol and glycerin, fillers, lubricants, wetting agents, flavoring agents, coloring agents, emulsifying, suspending or dispersing agents, suspending agents, sweeteners, etc. Preferably the extract is simply diluted with water and administered orally without any carriers or additives.

EXAMPLE 1

The xanthone derivative of Formula 1 was isolated and identified as follows.

The extraction method detailed above was used with mung bean as the raw material. A glass fiber membrane (80.9 g) was wetted with the resulting extract. The membrane was extracted with three 300 ml portions of a mixture of acetone and absolute ethanol (50% each). With each extraction, the solvent was removed and pooled together. The total extract was then evaporated to near dryness in a rotary evaporator using a vacuum at a temperature not exceeding 40° C. Upon evaporation, a pale yellow oil was obtained (8.1 g). The oil was then extracted with ethyl acetate (500 ml). The ethyl acetate layer was taken to dryness to give 0.61 g of crude material. This material chromatographed on Merck prepared silica gel plates using $CHCl_2/MeOH/H_2O$ (90:9.5–0.5) solvent system. The compound had an Rf value of 6.2. The compound was recrystallized from ethanol to provide needles. Upon air drying, the following were obtained:

| | |
|---|---|
| Melting point: | 192–193° C. |
| Molecular weight: | 293 |
| Carbon: | 69.62% |
| Hydrogen: | 3.75% |
| Oxygen: | 21.84% |
| Nitrogen: | 4.77% |

EXAMPLE 2

The extraction method detailed above was used with mung bean as the raw material. The membrane was a white clear looking short fiber glass wool. It was divided into two parts. The major part (60 g) was directly extracted with ethyl acetate (2×300 ml portions). The ethyl acetate was removed under vacuum. The temperature of the solvent layer did not exceed 40° C. The residue was a brown colored liquid (5.2 ml). This extract was then extracted with ethyl ether (100 ml). The ether layer was removed and concentrated by roto-evaporation under vacuum to give a white crystalline compound (2.0 mg).

An additional 60 g sample was fractionated by ethyl acetate extraction as above, except that after ethyl acetate extraction and concentration by rotary flask evaporation, the final extract (5.0 ml) was extracted with diethylether. The ether layer was dried by rotary evaporation to give 5.2 mg of a white tan crystallized compound. Further identity was determined by thin layer chromatography on Merck prepared silica gel plates using the following solvent system: $CHCH_2$—MEOH—$H_2O$ (90:9.5:0.5). The compound was visualized by spraying the plate lightly with a solution of 3% ceric sulfate in concentrated sulfuric acid. The plate was then heated to 150° C. for 10 minutes, cooled and visualized with ultraviolet light.

| Analysis: | |
|---|---|
| Absorption Spectra | 342 Peak |
| Thin layer chromatography | Rf 4.5 |
| Micro kjeldall | 12.1% |
| Melting Point | 160° C. |
| Amino Acid Sequence | Tyrosine-isoleucine-glycine-serine-arginine |

EXAMPLE 3

The extraction method detailed above was used with mung bean as the raw material. The membrane (50 g) was extracted with dichloromethane-methyl alcohol (1:1). 300 ml of this mixture was used. This gave a crude organic extract. It was taken to near dryness in a rotary evaporator, under reduced pressure. The maximum temperature of the extraction vessel was 40° C. A viscous, yellow oil was obtained. This weighed 2.40 g. To the viscous oil was added 100 ml of 80% MEOH, 20% $H_2O$. This was then extracted with 50 ml of chloroform. The chloroform layer was removed and taken to dryness. The resulting compound was recrystallized from ethanol to give needles. It was air-dried at room temperature.

| Analysis: | |
|---|---|
| Melting Point | 174–175° C. |
| Molecular weight | 196.10 |
| Carbon | 79.48% |
| Hydrogen | 4.10% |
| Oxygen | 16.31% |
| Identity of Compound | Xanthone ($C_{13}H_8O_2$) |

EXAMPLE 4

| Test Organisms: | |
|---|---|
| Species: | Mice |
| Strain: | Swiss-Webster |
| Supplier: | Animal Technologies Ltd., Kent, WA |
| Sex: | Female |
| Weight: | 26–30 |
| Number Used: | 20 |

| Husbandry | |
|---|---|
| Research Facility: | USDA Registration No. 91-R-043. NIH Public Health Assurance No. A3932-01 |
| Animal Rooms: | Light cycle-12 hours light, 12 hours dark. Temperature/Relative humidity: every attempt was made to maintain a temperature of 22° C. ± 3° C. and a relative humidity of 40 to 70% |
| Housing: | Mice were kept in groups of five in standard caging, in accordance with the "Guide for the Care and Use of Laboratory Animals" of the Institute of Laboratory Resources, National Research Council. |
| Sanitation: | Waste material was removed twice weekly. Cages and feeders were sanitized every two weeks. |
| Food: | Harlan Teklad Rodent Diet #8604 ad libitum |
| Food Analysis: | There are no contaminants that are reasonably expected to be present in the diet material known to be capable of interfering with the purpose or conduct of the study. |
| Water: | Availability - non-pyrogen deionized water. |
| Water Analysis: | The system is routinely maintained by Continental Water System Company every six months (change carbon tanks, D.I. beds and in-line filters). Replacement of the UF membranes is every 2 years, the UV lamp every year. |
| Test Article: | Isolate the compound from the membrane. |
| Dose Adminstration: | The test article dosing was an oral gavage for five days. The mice were sacrificed on Day 10. |
| Volume Administration Of Test Article: | 0.1 ml was administered by gavage. |

Assay Method

The compound obtained in Example 1 was dissolved in ethyl alcohol at 10 mg/ml. Dilutions of this stock solution were made to 100, 10 and 1 mcg per kilo body weight of the mice. The Sarcoma 180 assay was carried out as described below.

The tumor stock was a Sarcoma 180 which was started in the laboratory from an American Type Culture Collection. This stock culture has been passed at weekly intervals as an ascites in non-treated Swiss-Webster mice.

The current studies were all carried out with Swiss-Webster mice obtained from Animal Technologics Ltd., Kent, Wash. To prepare the inoculum, the ascites fluid from a mouse with a 7–10 day ascites is aspirated using a sterile technique. Once a cell count is established, the tumor cells are diluted with normal saline or phosphate buffered saline to obtain a final concentration of 1 to $2 \times 10^6$ cells per $mm^3$. This is the tumor suspension that is then injected into the mice. The final dilution is plated on trypticase soy agar to determine if it is free of contamination.

One tenth (0.1 ml) of the above suspension is inoculated into the left hind leg muscle (hamstring muscle mass) of each mouse. The inoculated mice are placed into one large cage and then randomly segregated into groups of five mice. The mice are housed in shoe box cages on wood shavings with free access to water and laboratory chow. The mice are weighed on the day of inoculation, on day 7, day 10, and at time of sacrifice.

Treatment of the mice was initiated the day after transplant and then continued for five days.

At the end of the observation period, 10 days, the mice are sacrificed either by cervical dislocation or ether anesthesia. The skin over the left hind leg is removed to expose the tumor and the leg and tumor are removed at the hip joint. Any residual skin is removed and the legs with tumors are weighed individually. Ten normal legs (right legs) are prepared in a similar manner and weighed. The mean value of the normal leg is subtracted from the weight of the leg with the tumor to give an estimate of the actual tumor weight.

$$\% \text{ Inhibition} = \frac{\text{Mean Tumor weight (test)}}{\text{Mean Tumor Weight (control)}} \times 100$$

| Dose | 1 mcg/kg | 10 mcg/kg | 100 mcg/kg | Control |
|---|---|---|---|---|
| % Tumor Inhibition | 43 | 100 | 100 | 0 |
| Body wt. G (avg.) | 27.88 | 28.3 | 27.78 | 29.22 |

As the data show, the xanthone derivative tested is extremely active in the inhibition of Sarcoma 180 in the mouse model as indicated in the dosage schedule. No toxicity was shown at any dose, as indicated by the body weights.

References:

Geran, P. I., Greenberg, N. H., MacDonald, M. M., Schumaker, A. M., Abbott, B. J., Protocols for screening chemical agents and natural products against animal tumors and other biological systems. Cancer Chemotherap. Rep. 1972, 3. (Part 3), 1–103.

J. R. Tennant, Evaluation of the trypan-blue technique for the determination of cell viability. Transplantation 1964, 2, 685–694.

EXAMPLE 5

| Test Organisms | |
|---|---|
| Species: | Mice |
| Strain: | Swiss-Webster |
| Supplier: | Animal Technologies Ltd., Kent, WA |
| Sex: | Female |
| Weight: | 26–30 |
| Number Used: | 15 |

| Husbandry | |
|---|---|
| Research Facility: | USDA Registration No. 91-R-043. NIH Public Health Assurance No. A3932-01 |
| Animal Rooms: | Light cycle-12 hours light, 12 hours dark. Temperature/Relative humidity: every attempt was made to maintain a temperature of 22° C. ± 3° C. and a relative humidity of 40 to 70%. |
| Housing: | Mice were kept in groups of five in standard caging, in accordance with the "Guide for the Care and Use of Laboratory Animals" of the Institute of Laboratory Resources, National Research Council. |
| Sanitation: | Waste material was removed twice weekly. Cages and feeders were sanitized every two weeks. |
| Food: | Harlan Teklad Rodent Diet #8604 ad libitum. |
| Food Analysis: | There are no contaminants that are reasonably expected to be present in the diet material known to be capable of interfering with the purpose or conduct of the study. |
| Water: | Availability - non-pyrogen deionized water. |
| Water Analysis: | The system is routinely maintained by Continental Water System Company every six months (change carbon tanks, D.I. beds and in-line filters). Replacement of the UF membranes is every 2 years, the UV lamp every year. |
| Test Article: | Isolates from the compound. |
| Dose Administration: | The test article dosing was an oral dose. |
| Volume Administration Of Test Article: | 0.1 ml was administered by gavage. |

Assay Method

The compound obtained in Example 1 was dissolved in ethyl alcohol at 10 mg/ml. Dilutions of this stock solution were made to 100, 10 and 1 mcg per kilo body weight of the mice. The Sarcoma 180 assay was carried out as described below.

The tumor stock was a Sarcoma 180, which was started in the laboratory from an American Type Culture Collection. This stock culture has been passed at weekly intervals as an ascites in non-treated Swiss-Webster mice.

The current studies were all carried out with Swiss-Webster mice obtained from Animal Technologics Ltd., Kent, Wash. To prepare the inoculum, the ascites fluid from a mouse with a 7–12 day ascites is aspirated using a sterile technique. The tumor cells are checked for viability using the trypan-blue staining technique. Once a cell count is established, the tumor cells are diluted with normal saline or phosphate buffered saline to obtain a final concentration of 1 to $2 \times 10^6$ cells per $mm^3$. This is the tumor suspension that is then injected into the mice. The final dilution is plated on trypticase soy agar to determine if it is free of contamination.

One tenth (0.1 ml) of the above suspension is inoculated into the left hind leg muscle (hamstring muscle mass) of each mouse. The inoculated mice are placed into one large cage and then randomly segregated into groups of five mice. The mice are housed in shoe box cages on wood shavings with free access to water and laboratory chow. The mice are weighed on the day of inoculation, on day 7, day 12, and at time of sacrifice.

Treatment of the mice was initiated the day after transplant. The treatment period was 12 days.

At the end of the observation period, the mice are sacrificed by ether anesthesia. The skin over the left hind leg is removed to expose the tumor and the leg and tumor are removed at the hip joint. Any residual skin is removed and the legs with tumors are weighed individually. Ten normal legs (right legs) are prepared in a similar manner and weighed. The mean value of the normal leg is subtracted from the weight of the leg with the tumor to give an estimate of the actual tumor weight.

$$\% \text{ Inhibition} = \frac{\text{Mean Tumor weight (test)}}{\text{Mean Tumor Weight (control)}} \times 100$$

Results:

| Dose | 1 mcg/kg | 10 mcg/kg | Control |
|---|---|---|---|
| % Tumor Inhibition | 98.5* | 100* | 0 |
| Body wt. G (avg.) | 29.2 | 28.7 | 29.4 |

*No sign of tumor was seen in any of the mice.

As the data show, the derivative tested is extremely active in the inhibition of Sarcoma 180 at 1 microgram per kilo body weight. There was no visible tumor seen. The control animal fed the similar amount of distilled water all had tumors weighing an average of 1.66 g ±0.2 g. The final body weights of the mice in all three groups were comparable, indicating that the treatment was not toxic.

References:

Geran, P. I., Greenberg, N. H., MacDonald, M. M., Schumaker, A. M., Abbott, B. J., Protocols for screening chemical agents and natural products against animal tumors and other biological systems. Cancer Chemotherap. Rep. 1972, 3. (Part 3), 1–103.

J. R. Tennant, Evaluation of the trypan-blue technique for the determination of cell viability. Transplantation 1964, 2, 685–694.

EXAMPLE 6

Protocol Design

An adjuvant-induced arthritis model developed using rats has been shown to allow screening of compounds that may be useful in the treatment of rheumatoid arthritis in man. Adjuvant-induced arthritis responds to both steroids and non-steroids. The degree of inflammation is assessed by measuring differences in foot weight and/or the foot volume.

Test Organism

Rats weighing between 150–200 g were purchased from ATL, in Kent Wash. They were male Sprague-Dawley rats. The animals were kept individually in stainless steel cages with free access to water and feed (Harlan Teklan Rodent Diet). The light cycle was maintained at 12 hours light and 12 hours dark. The temperature was maintained at 22° C.±3° C. with a relative humidity of 40 to 70%.

Dose Administration:

The test materials were dissolved in deionized water at the doses of 1 mcg/kg body weight. The test compound and hydrocortisone were given by gavage.

Test Duration:

The test materials were delivered orally (by gavage) once per day for 7 days.

Experimental Design

Male Sprague-Dawley rats (150–200 g) were sensitized by injecting Fruend's complete adjuvant (0.5% suspension of killed mycobacterium tuberculosis (H37RA, Difco, in mineral oil)). A 0.1 ml aliquot was administered intradermally at a plantar site on the right hind leg of each rat.

The test materials were given orally (by gavage) to each of 5 rats per treatment group once per day for 7 days. Administration of the test materials was initiated on the day of sensitization.

The left hind paw was measured just before sensitization an again on Day 7. The plantar edema inhibitory rate and the body weight gain were determined by comparison with the non-sensitized rat groups.

The paw weights for each rat group were averaged. Anti-inflammatory activity was determined by comparing paw weights calculated as follows:

$$\% \text{ Anti-inflammatory response} = \frac{\text{Mean paw wts. of controls} - \text{Mean paw wts. of test } qp.}{\text{Mean paw weight of test group}} \times 100$$

Results:

TABLE 1

Comparison of Compound to hydrocortisone in the rat adjuvant arthritis assay (five rats per group)

|  | Rat paw wt., g | % Inhibition |
|---|---|---|
| Control, No treatment, water | 1.276 | — |
| 10 mg/kg body wt., hydrocortisone | 0.98 | 42.0 |
| 1 mcg/kg body wt., inventive compound | 0.324 | 95.2 |

The compound of the invention was a very effective anti-inflammatory agent in the rat adjuvant arthritis assay. At 1 mcg/kg body weight, it produced 95.2% inhibition of rat paw inflammation compared to 42% for 10 mg/kg body weight hydrocortisone.

TABLE 2

Comparison of Compound to hydrocortisone in the rat adjuvant arthritis assay (five rats per group)

|  | Avg. Initial Body wt., g | Avg. Final Body wt., g | Avg. Rat wt. Gain, g |
|---|---|---|---|
| Control, No treatment, water | 154.4 | 181.8 | +27.4 |
| 10 mg/kg body wt., hydrocortisone | 155.8 | 166.0 | +10.4 |
| 1 mcg/kg body wt., inventive compound | 155.4 | 182.4 | +27 |

Comparison was made of the body weight gains of the three groups in Table 2. The weight gains of the control group versus the inventive compound were 27.14 and 27.0, respectively. The hydrocortisone group treated at 10 mg/kg body weight had a weight gain of only 10.4 grams per rat. On the basis of weight gain, there is no apparent toxicity in this 7-day treatment period.

EXAMPLE 7

| Test Organisms | |
| --- | --- |
| Species: | Mice |
| Strain: | Swiss-Webster |
| Supplier: | Animal Technologies Ltd., Kent, WA |
| Sex: | Female |
| Weight: | 26–30 |
| Number Used: | 30 |

| Husbandry | |
| --- | --- |
| Research Facility: | USDA Registration No. 91-R-043. NIH Public Health Assurance No. A3932-01 |
| Animal Rooms: | Light cycle-12 hours light, 12 hours dark. Temperature/Relative humidity: every attempt was made to maintain a temperature of 22° C. ± 3° C. and a relative humidity of 40 to 70%. |
| Housing: | Mice were kept in groups of five in standard caging, sized in accordance with the "Guide for the Care and Use of Laboratory Animals" of the Institute of Laboratory Resources, National Research Council. |
| Sanitation: | Waste material was removed twice weekly. Cages and feeders were sanitized every two weeks. |
| Food: | Harlan Teklad Rodent Diet #8604 ad libitum. |
| Food Analysis: | There are no contaminants that are reasonably expected to be present in the diet material known to be capable of interfering with the purpose or conduct of the study. |
| Water: | Availability - non-pyrogen deionized water. |
| Water Analysis: | The system is routinely maintained by Continental Water System Company every six months (change carbon tanks, D.I. beds and in-line filters). Replacement of the UF membranes is every 2 years, the UV lamp every year. |
| Test Article: | Isolates of the compound from the membrane. |
| Dose Administration: | The test article dosing was an single intraperitoneal dose. |
| Volume Administration Of Test Article: | 0.1 ml was administered by intraperitneal injection. |

Assay Method

The tumor stock was a Sarcoma 180 which was started in the laboratory from an American Type Culture Collection. This stock culture has been passed at weekly intervals as an ascites in non-treated Swiss-Webster mice.

The current studies were all carried out with Swiss-Webster mice obtained from Animal Technologics Ltd., Kent, Wash. To prepare the inoculum, the ascites fluid from a mouse with a 7–10 day ascites is aspirated using a sterile technique. Once a cell count was established, the tumor cells were diluted with normal saline or phosphate buffered saline to obtain a final concentration of 1 to $2 \times 10^6$ cells per $mm^3$. This was the tumor suspension that was then injected into the mice. The final dilution was plated on trypticase soy agar to determine if it was free of contamination.

One tenth (0.1 ml) of the above suspension was inoculated into the left hind leg muscle (hamstring muscle mass) of each mouse. The inoculated mice were placed into one large cage and then randomly segregated into groups of five mice. The mice were housed in shoe box cages on wood shavings with free access to water and laboratory chow. The mice were weighed on the day of inoculation, on day 7, day 10, and at time of sacrifice.

Treatment of the mice was initiated the day after transplant. At the end of the observation period, the mice were sacrificed by ether anesthesia. The skin over the left hind leg was removed to expose the tumor and the leg and tumor were removed at the hip joint. Any residual skin was removed and the legs with tumors were weighed individually. Ten normal legs (right legs) were prepared in a similar manner and weighed. The mean value of the normal leg was subtracted from the weight of the leg with the tumor to give an estimate of the actual tumor weight:

$$\% \text{ Inhibition} = \frac{\text{Mean Tumor weight (test)}}{\text{Mean Tumor Weight (control)}} \times 100$$

| | Control | Compound of Example 2 |
| --- | --- | --- |
| Net Tumor weight, g | 1.39 | 0 |
| % Tumor Inhibition | — | 100% |

At 1 mg/kg body weight in a single intraperitoneal injection, the Sarcoma 180 was completely inhibited.

| | Control No Treatment | 1 mg/kg Compound of Example 3 | 10 mg/kg Compound of Example 3 | 100 mg/kg Compound of Example 3 |
| --- | --- | --- | --- | --- |
| Net Tumor wt. | 1.5 g | 0.3 g | 0 | 0 |
| % Inhibition | — | 80% | 100% | 100% |

The compound of Example 3 was injected in a single dose intraperitoneally. Mice treated at 10 and 100 mg/kg body weight showed no evidence of tumor.

Body Weights:

The body weights of the mice were recorded on Day 1, 7 and 10. At the doses used, there were no weight losses seen in any of the groups. The lack of weight loss in the reated animals indicates low or no toxicity.

COMPOUND OF EXAMPLE 2:

| | Peptide Control | Peptide Treated |
| --- | --- | --- |
| Day 1 | 24.9 | 25.1 |
| Day 7 | 25.6 | 26.1 |
| Day 10 | 26.1 | 26.2 |

COMPOUND OF EXAMPLE 3:

| | Control | 1 mg/kg | 10 mg/kg | 100 mg/kg |
| --- | --- | --- | --- | --- |
| Day 1 | 23.4 | 24.2 | 23.8 | 23.4 |
| Day 7 | 25.9 | 26.0 | 26.1 | 26.2 |
| Day 10 | 25.8 | 26.2 | 26.4 | 26.5 |

What is claimed is:

1. A xanthone derivative of the following formula:

or a tautomer, enantiomer or stereoisomer thereof, or a physiologically acceptable salt or solvate therefor or mixtures thereof.

2. A pharmaceutical composition comprising a compound, salt or solvate according to claim 1 and a pharmaceutically acceptable carrier.

3. A method of preparing a compound according to claim 1, comprising extracting from mung bean an extract by the following method:
   heating water to a predetermined temperature;
   atomizing said heated water into minute particles;
   contacting said mung bean under a state of decompression with said heated and atomized water particles;
   condensing the resulting water particles;
   collecting the resulting cooled water; and solidifying the resulting liquid extract by the following method:
   providing an absorbent;
   contacting said absorbent material with said extract; and
   drying the resultant wetted absorbent material to produce a solid form of said extract; and isolating a solution comprising said compound, xanthone and a peptide having the amino acid sequence Tyrosine-isoleucine-glycine-serine-arginine from said extract.

4. The method of claim 3, wherein said absorbent material comprises glass fiber.

5. The method of claim 3, wherein said drying is freeze-drying.

6. The method of claim 5, wherein said freeze drying is carried out at a temperature ranging from about −10° C. to about −70° C.

7. A pharmaceutical composition comprising an extract comprising xanthone, a peptide having the amino acid sequence Tyrosine-isoleucine-glycine-serine-arginine, and a xanthone derivative or a tautomer, enantiomer or stereoisomer thereof having the following formula:

or physiologically acceptable salts or solvates therefore, together with a pharmaceutically acceptable carrier.

* * * * *